US005730965A

United States Patent [19]
Rapaport

[11] Patent Number: 5,730,965
[45] Date of Patent: Mar. 24, 1998

[54] SHAMPOO FOR TREATING SEBORRHEIC DERMATITIS, DANDRUFF OR PSORIASIS

[75] Inventor: Jeffrey Rapaport, Fort Lee, N.J.

[73] Assignee: Dermatology Home Products, Inc., Fort Lee, N.J.

[21] Appl. No.: 662,989

[22] Filed: Jun. 13, 1996

[51] Int. Cl.$^6$ .................................................. A61K 7/06
[52] U.S. Cl. ................ 424/70.1; 424/70.19; 424/70.21; 424/70.24; 424/70.11; 424/195.1; 424/60; 424/63; 424/65; 514/887; 514/852
[58] Field of Search .................... 424/70.19, 70.21, 424/70.24, 70.1, 195.1, 60, 63, 65; 514/852, 887

[56] References Cited

U.S. PATENT DOCUMENTS

| | | | |
|---|---|---|---|
| 4,569,935 | 2/1986 | Rosenberg et al. | 514/252 |
| 4,745,103 | 5/1988 | Oono et al. | 514/23 |
| 4,834,076 | 5/1989 | Millet et al. | 128/65 |
| 4,874,361 | 10/1989 | Obagi | 424/101 |
| 4,942,162 | 7/1990 | Rosenberg et al. | 514/252 |
| 4,963,591 | 10/1990 | Fourman | 514/944 |
| 5,370,875 | 12/1994 | Rogozinski | 424/405 |
| 5,384,114 | 1/1995 | Dowell et al. | 424/70.1 |
| 5,384,134 | 1/1995 | Kross et al. | 424/661 |
| 5,403,864 | 4/1995 | Bruch et al. | 514/721 |
| 5,587,154 | 12/1996 | Dowell et al. | 424/70.11 |

OTHER PUBLICATIONS

"Announcing Two Improvements in Head & Shoulders®", advertisement, Head & Shoulders® shampoo, Procter & Gamble, 1995.

Samuel L. Moschella, M.D. et al., "*Dermatology*", Papulosquomous Eruptions and Exfoliative Dermatitis, W.B. Saunders Co., Third Edition, pp. 610–611, 1992.

"Diagnosis and Management of Cutaneous Fungal Infections", *Clinical Mycology Update*, pp. 1–8, May 1995.

*International Congress and Symposium Series*, No. 132, Royal Society of Medicine Services, "Seborrheic Dermatitis and Dandruff –A fungal Disease", 1988: Articles include: S. Shuster, Introduction: a history, pp. 1–4; P.M. Farr, Initial Studies on the Treatment of Seborrheic Dermatitis with Oral Ketoconazole, pp. 5–11; R.J. Hat et al, Pathogenic Mechanisms of Pityrosporum Infection, pp. 13–19; F.A. Ive, The Treatment of Seborrheic Dermatitis and Dandruff with Topical Ketoconazole, pp. 21–27; N.R. Blatchford, The Pharmacokinetics of Oral and Topical Ketoconazole, pp. 29–34; G. Cauwenbergh, International Experience with Ketoconzole Shampoo in the Treatment of Sebborheic Dermatitis and Dandruff, pp. 35–45; J.Faergemann, The Antifungal Activities of Ketoconazole and Itraconzole Against Pityrosporum Orbiculare Treated in Vitro and in a Rabbit Model, pp. 47–52; and S. Shuster, Summary, pp. 53–54.

*Primary Examiner*—Thurman K. Page
*Assistant Examiner*—D. Faulkner
*Attorney, Agent, or Firm*—Alfred M. Walker

[57] ABSTRACT

A method is provided to treat and/or prevent seborrheic dermatitis of the scalp and other hair bearing areas, dandruff or psoriasis by topically applying to the skin and washing the skin in a shampoo containing an effective amount of a treatment composition containing chloroxylenol, preferably by daily application in a pharmaceutically acceptable vehicle at a concentration of from 0.1 to five (5) percent by weight, preferably about one (1) percent by weight.

5 Claims, No Drawings

SHAMPOO FOR TREATING SEBORRHEIC DERMATITIS, DANDRUFF OR PSORIASIS

FIELD OF THE INVENTION

The present invention is directed to a method of treating seborrheic dermatitis of the scalp and other hair bearing areas, dandruff or psoriasis.

BACKGROUND OF THE INVENTION

Treatment of seborrheic dermatitis and dandruff has been discussed in the prior art. Among the most common treatment regimen is a shampoo with zinc pyrithione as an active ingredient, such as discussed in "Announcing Two improvements in Head & Shoulders®", a 1995 advertisement publication of Procter & Gamble, the manufacturer of Head & Shoulders® shampoo.

Samuel L. Moschella, M.D. et al. in *"Dermatology"*, in a chapter entitled "Papulosquamous Eruptions and Exfoliative Dermatitis" W. B. Saunders Company, Third Edition, pgs. 610–611, 1992 states that microbiological studies have revealed that skin conditions such as psoriasis are associated with increased numbers of *Staphylococcus aureus* bacteria, and that improvements in psoriatic skin lesions are noticed when topical and systemic antibiotics are administered.

In "Diagnosis and Management of Cutaneous Fungal Infections", *Clinical Mycology Update*, pgs. 1–8, May 1995; it was shown that seborrheic dermatitis is increased in persons with yeast infections and that treatment with shampoos having anti-fungal agents such as ketoconazole reduces scalp fungi and clinical symptoms of seborrheic dermatitis and dandruff.

Articles in the *International Congress and Symposium Series*, Number 132, Royal Society of Medicine Services, 1988: "Seborrheic dermatitis and dandruff—a fungal disease" discuss the use of anti-fungal agents such as ketoconazole in treating scalp and other skin seborrheic dermatitis and dandruff. Among the articles include, S. Shuster, "Introduction: a history", pgs. 1–4; P. M. Farr, "Initial studies on the treatment of seborrheic dermatitis with oral ketoconazole", pgs. 5–11; R. J. Hay et al., "Pathogenic mechanisms of Pityrosporum infection", pgs. 13–19; F. A. Ive, "The treatment of seborrheic dermatitis and dandruff with topical ketoconazole", pgs. 21–27; N. R. Blatchfold, "The pharmacokinetics of oral and topical ketoconazole", pgs. 29–34; G. Cauwenbergh, "International experience with ketoconazole shampoo in the treatment of seborrheic dermatitis and dandruff, pgs. 35–45; J. Faergemann, "The antifungal activities of ketoconazole and itraconazole against *Pityrosporum orbiculare* treated in vitro and in a rabbit model", pgs. 47–52; and S. Shuster, "Summary", pgs. 53–54.

U.S. Pat. No. 5,370,875 of Rogozinski describes dry topical antimicrobial powders including chloroxylenol and chlorhexidine diacetate for treating skin fungal and bacterial induced conditions. However, Rogozinski does not describe or suggest the use of chloroxylenol in a shampoo for treating seborrheic dermatitis and dandruff.

U.S. Pat. No. 5,403,864 of Brunch describes a rapidly-acting topical alcohol based antimicrobial composition using triclosan and chloroxylenol.

U.S. Pat. No. 5,384,134 of Kross describes anti-inflammatory formulations for skin inflammatory diseases.

U.S. Pat. No. 4,569,935 of Rosenberg describes a topical treatment of psoriasis with imidazole antibiotics, and U.S. Pat. No. 4,942,162, also of Rosenberg, describes a topical treatment of seborrheic dermatitis with the anti-fungal agent ketoconozole and coal tar. However, because the anti-fungal agents in Rosenberg '162 are insoluble in water, they are not effective in penetrating the skin in combination with water based shampoos.

U.S. Pat. No. 4,745,103 of Oono describes hair cosmetic compositions with aliphatic hydrocarbons and alcohol.

U.S. Pat. No. 4,834,076 of Millet describes a device for treating the external human epithelium and a process for its manufacture and process for using such a device in a comb coated with slow release active skin treating substances, including chloroxylenol. However the delivery regimen is by slow release encapsulations on the comb bristles, not in a shampoo.

However, when used in the prior art, chloroxylenol is presented in alcohol based solutions, topical creams and lotions, or in the slow release encapsulations of the comb of Millet '076.

Moreover, in prior art shampoos, the active ingredients such as coal tar, zinc pyrithione and selenium selide do not work as well as the chloroxylenol-based shampoo of the present invention in reducing the effects of seborrheic dermatitis and/or dandruff flakes because they do not elicit an effective response in the epidermis and dermis and hair follicles, because chloroxylenol is more fat soluble in the fatty acid components of shampoo than traditional components which are not as soluble in fat. Therefore, traditional shampoo components, such as zinc pyrithione, selenium or coal tar do not penetrate the skin as well.

OBJECTS OF THE INVENTION

It is therefore an object of the present invention to provide an effective treatment for psoriasis, seborrheic dermatitis and resultant dandruff and itching sequelae.

It is yet another object to provide a shampoo for more effective treatment of psoriasis, seborrheic dermatitis and resultant dandruff and itching sequelae.

It is yet a further object to provide a shampoo wherein the active ingredient is antimicrobial.

It is yet a further object to provide a shampoo wherein the anti-microbial active ingredient is soluble in fatty acids of a shampoo for better penetration to the skin during a shampoo wash.

It is yet another object to improve over the disadvantages of the prior art.

BRIEF SUMMARY OF THE INVENTION

In keeping with these objects and others which may become apparent, according to the present invention, a method is provided for preventing and/or treating seborrheic dermatitis of the scalp and other hair bearing areas, dandruff or psoriasis, by topical application of a shampoo, preferably a composition containing effective amounts of chloroxylenol to the affected area of the skin. The chloroxylenol is applied in a pharmaceutically acceptable vehicle, such as a shampoo or hair rinse, in a concentration of from at least 0.1 percent, to five (5) percent by weight, preferably about one (1) percent by weight, generally by frequent periodic application, such as once or twice daily application.

Tests on humans show that topical application of a pharmaceutically acceptable composition containing from about 0.1 to five (5) percent of chloroxylenol prevents or reduces seborrheic dermatitis or scalp dandruff. Tests also show that when such compositions are applied, the dandruff flakes decrease and the skin becomes less itchy.

Chloroxylenol shampoo treatment compositions work in reducing the effects of seborrheic dermatitis and/or dandruff flakes because chloroxylenol penetrates the epidermism, dermis and the hair follicles of the skin better than conventional shampoo treatments, such as selenium, zinc pyrithione or coal tar, because chloroxylenol is more fat soluble in the fatty acids of shampoo.

DETAILED DESCRIPTION OF THE PREFERRED EMBODIMENTS

In accordance with the present invention, a method is provided for the prevention and/or treatment of seborrheic dermatitis of the scalp and other hair bearing areas, dandruff or psoriasis which may accompany this skin condition. The method comprises the topical application of suitable compositions containing chloroxylenol. The topical application to the skin of a user, may be by a shampoo or hair rinse.

In general, the treatment composition suitable for use in accordance with the invention containing chloroxylenol, may be applied in any dermatological acceptable vehicle such as a gel, lotion or cream base. Other suitable formulations will be apparent to those skilled in the art.

In the present invention, the method for the prevention and/or treatment of seborrheic dermatitis of the scalp and other hair bearing areas, dandruff or psoriasis is by application of a shampoo containing chloroxylenol in a concentration of chloroxylenol of from 0.1 to about five (5) percent by weight of the total composition, and preferably about one (1) percent by weight of the composition.

Treatment compositions containing concentrations up to about thirty (30) percent by weight of chloroxylenol thereof will not cause any appreciable side effects.

Chloroxylenol suitable for use in the treatment compositions of the invention will improve the condition of the skin and hair to which it is applied, preferably by frequent periodical application over an extended period of time without undue irritation to the skin or any other side effects.

The topical preparation described above is formulated in any suitable topical hair and skin care carrier such as a shampoo, cream, shaving cream, lotion, gel, which may or may not be emulsified and may contain ingredients to improve, modify, or stabilize the formulation physically or cosmetically. These ingredients may include (in any combination), but are not limited to:

a) chloroxylenol;

b) alpha hydroxy acids, such as glycolic acid;

c) salicylic acid;

d) a diluent, vehicle, extender or base such as water, alcohol, propylene glycol, oils, petrolatum, polyhydrics, and the like;

e) a gelling or viscosity modifying system which may include fats, synthetic waxes and oils gums, resins, clays, gases, colloidal gellants or modifiers, and the like;

f) preservatives to inhibit or prevent microbiological contamination;

g) anti-oxidants, vitamins, minerals, botanical or animal extracts to protect the formulation from degradation and extend shelf life to enhance the performance of the product;

h) anti-oxidants, vitamins, minerals, botanical or animal extracts to protect, prepare, or mediate the action of the product on the dermis, by interaction with the product of the dermis or both, and, i) shampoo components such as sodium laureth sulfate, sodium lauryl sulfate, ammonium lauryl sulfate, ammonium laureth sulfate, ammonium xylenesulfate, ammonium chloride, dipropylene glycol, methyldibromo glutaronitrile, benzophenome-4, magnesium aluminum silicate, cocamide DEA, cocamidopropyl betaine, hexylene glycol, methylparaben, propylparaben, hydroxypropyl methylcellulose, tetrasodium EDTA, citric acid, hydrolized soy protein, and related fragrances and colors.

The treatment compositions used in the practice of the invention are intended to be applied to and subsequently removed by shampoo washing, rinsing, or the like.

Generally, the topical applications are applied periodically such as one or two times per day. Significant clinical improvement may be observed after two (2) to four (4) weeks of daily treatment, wherein the extent of seborrheic dermatitis rash and/or dandruff flakes are substantially reduced, with a relief of itching.

Suitable chloroxylenol shampoo treatment compositions work in reducing the effects of seborrheic dermatitis and/or dandruff flakes by virtue of chloroxylenol eliciting a response in the epidermis and dermis and penetrates the hair follicle better than conventional shampoo treatments, such as selenium, zinc pyrithione or coal tar, because chloroxylenol is more fat soluble in the fatty acid components of shampoo than traditional components which are not as soluble in fat. Therefore, traditional shampoo components, such as zinc pyrithione, selenium or coal tar do not penetrate the skin as well.

Compositions that may be applied in accordance with the method of treatment of seborrheic dermatitis of the present invention are illustrated by the following typical cosmetically acceptable compositions for topical application to human skin.

EXAMPLE

The following illustrates a topically applied skin cream which can be prepared using conventional procedures from the following ingredients with typical ranges of acceptable percentages by weight and typical preferred percentage by weight shown.

|  | Minimal (% w/w) | Usage Range (% w/w) | Maximum (% w/w) | Preferred (% w/w) |
|---|---|---|---|---|
| Purified Water |  | Bal. to 100% |  |  |
| Gycolic Acid | 0.0 | .1–30 | 30 | 10 |
| Salicylic Acid | 0.0 | .1–6 | 6 | 3 |
| Strong Ammonia Solution NF | 0.0 | .1–40 | 40 | 5 |
| Ammonium Lauryl Sulfate | 0.0 | .1–75 | 75 | 20 |
| Sodium Laureth Sulfate | 0.0 | .1–75 | 75 | 5 |
| Cocamidopropyl Betaine | 0.0 | .1–75 | 75 | 5 |
| Glycol Distearate | 0.0 | 1–10 | 10 | 2 |
| Cocamide DEA | 0.0 | .1–10 | 10 | 2 |
| Chloroxylenol | 0.1 | .1–5 | 5 | 1 |
| Yucca Extract | 0.0 | .1–75 | 75 | 1 |
| Fragrance | 0.0 | 0–10 | 10 | 0.5 |

TEST RESULTS

To study the beneficial results of the treating composition of the present invention, a number of patients were treated for seborrheic dermatitis, dandruff and psoriasis, using a shampoo with chloroxylenol. In each case, significant lightening of skin rash and dandruff flakes were noted.

| Patent | Description | Condition(s) Treated | Regimen |
|---|---|---|---|
| CG Pat. No. 1 | 40 yr. old male | seborrheic dermatitis and psoriasis | 3 weeks of shampoo every night |
| EL Pat. No. 2 | 34 yr. old male | seborrheic dermatitis and folliculitis | 2 weeks of shampoo every night |
| KB Pat. No. 3 | 35 yr. old male | psoriasis | 6 weeks of shampoo every night |
| KM Pat. No. 4 | 25 yr. old female | psoriasis | 3 weeks of shampoo every night |

CONCLUSIONS

Shampoos containing an effective amount of chloroxylenol were effective in reducing seborrheic dermatitis and psoriasis of the scalp and other hair bearing areas.

Other changes to the present invention may be made without departing from the spirit or scope thereof when read in conjunction with the appended claims.

I claim:

1. A method of treating seborrheic dermatitis of the scalp and other hair bearing areas, dandruff or psoriasis, comprising topically applying to the area of the skin affected with a composition as follows:

| Component | Usage Range (% w/w) |
|---|---|
| Purified Water | Balance to 100% |
| Glycolic Acid | 0–30 |
| Salicylic Acid | .1–6 |
| Strong Ammonia Solution NF | 0–40 |
| Ammonium Lauryl Sulfate | 0–75 |
| Sodium Laureth Sulfate | 0–75 |
| Cocamidopropyl Betaine | 0–75 |
| Glycol Distearate | 0–10 |
| Cocamide DEA | 0–10 |
| Chloroxylenol | .1–5 |
| Yucca Extract | 0–75 |
| Fragrance | 0–10 |

2. The method of treating seborrheic dermatitis of the scalp and other hair bearing areas, dandruff or psoriasis, as in claim 1, wherein the composition applied topically to the skin affected comprises as follows:

| Component | Preferred (% w/w) |
|---|---|
| Purified Water | Balance to 100% |
| Salicylic Acid | about 3 |
| Strong Ammonia Solution NF | about 5 |
| Ammonium Lauryl Sulfate | about 20 |
| Sodium Laureth Sulfate | about 5 |
| Cocamidopropyl Betaine | about 5 |
| Glycol Distearate | about 2 |
| Cocamide DEA | about 2 |
| Chloroxylenol | about 1 |
| Yucca Extract | about 1 |
| Fragrance | about 0.5. |

3. A shampoo composition for treating seborrheic dermatitis of the scalp and other hair bearing areas, dandruff or psoriasis, comprising:

| Component | Usage Range (% w/w) |
|---|---|
| Purified Water | Balance to 100% |
| Glycolic Acid | 0–30 |
| Salicylic Acid | .1–6 |
| Strong Ammonia Solution NF | .1–40 |
| Ammonium Lauryl Sulfate | .1–75 |
| Sodium Laureth Sulfate | .1–75 |
| Cocamidopropyl Betaine | .1–75 |
| Glycol Distearate | 1–10 |
| Cocamide DEA | .1–10 |
| Chloroxylenol | .1–5 |
| Yucca Extract | .1–75 |
| Fragrance | 0–10. |

4. The shampoo composition for treating seborrheic dermatitis of the scalp and other hair bearing areas, dandruff or psoriasis, as in claim 3, wherein the composition comprises as follows:

| Component | Preferred (% w/w) |
|---|---|
| Purified Water | Balance to 100% |
| Salicylic Acid | about 3 |
| Strong Ammonia Solution NF | about 5 |
| Ammonium Lauryl Sulfate | about 20 |
| Sodium Laureth Sulfate | about 5 |
| Cocamidopropyl Betaine | about 5 |
| Glycol Distearate | about 2 |
| Cocamide DEA | about 2 |
| Chloroxylenol | about 1 |
| Yucca Extract | about 1 |
| Fragrance | about 0.5. |

5. A shampoo composition for treating seborrheic dermatitis of the scalp and other hair bearing areas, dandruff or psoriasis, comprising:

| Component | Usage Range (% w/w) |
|---|---|
| Purified Water | Balance to 100% |
| Glycolic Acid | 0–30 |
| Salicylic Acid | .1–6 |
| Strong Ammonia Solution NF | 0–40 |
| Ammonium Lauryl Sulfate | 0–75 |
| Sodium Laureth Sulfate | 0–75 |
| Cocamidopropyl Betaine | 0–75 |
| Glycol Distearate | 0–10 |
| Cocamide DEA | 0–10 |
| Chloroxylenol | .1–5 |
| Yucca Extract | 0–75 |
| Fragrance | 0–10. |

* * * * *